US007010355B2

(12) United States Patent
Lee

(10) Patent No.: US 7,010,355 B2
(45) Date of Patent: Mar. 7, 2006

(54) METHOD AND APPARATUS FOR CONNECTING VARIOUS IMPLANTABLE MEDICAL TREATMENT SYSTEM COMPONENT DEVICES

(75) Inventor: David Warren Lee, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 282 days.

(21) Appl. No.: 10/098,279

(22) Filed: Mar. 15, 2002

(65) Prior Publication Data

US 2003/0176906 A1 Sep. 18, 2003

(51) Int. Cl.
*A61N 1/10* (2006.01)

(52) U.S. Cl. .................................................... 607/60

(58) Field of Classification Search ........ 607/115–118, 607/60, 30–37, 9; 128/899; 439/577, 578; 285/243
See application file for complete search history.

(56) References Cited

U.S. PATENT DOCUMENTS

| 4,066,086 A | | 1/1978 | Alferness et al. |
| 4,301,804 A | | 11/1981 | Thompson et al. |
| 4,419,996 A | * | 12/1983 | Tarjan ........................ 607/30 |
| 4,532,931 A | * | 8/1985 | Mills ........................... 607/9 |
| 4,726,378 A | * | 2/1988 | Kaplan ........................ 607/115 |
| 4,963,105 A | * | 10/1990 | Lewis et al. ................ 439/578 |
| 5,292,343 A | | 3/1994 | Blanchette et al. |
| 5,324,311 A | * | 6/1994 | Acken ........................ 607/37 |
| D359,803 S | | 6/1995 | Stanton et al. |
| 5,431,509 A | | 7/1995 | Anderson |
| D361,555 S | | 8/1995 | Erickson et al. |
| 5,529,578 A | | 6/1996 | Struble |
| 5,557,210 A | | 9/1996 | Cappa et al. |
| 5,558,640 A | | 9/1996 | Pfeiler et al. |
| 5,679,022 A | | 10/1997 | Cappa et al. |
| 5,735,887 A | * | 4/1998 | Barreras et al. ............. 607/60 |
| 5,820,589 A | | 10/1998 | Torgerson et al. |
| 5,999,857 A | | 12/1999 | Weijand et al. |
| 6,093,167 A | | 7/2000 | Houben et al. |
| 6,115,623 A | | 9/2000 | McFee et al. |
| 6,135,978 A | | 10/2000 | Houben et al. |
| 6,249,703 B1 | | 6/2001 | Stanton et al. |
| 6,261,280 B1 | | 7/2001 | Houben et al. |
| 6,263,246 B1 | | 7/2001 | Goedeke et al. |
| 6,292,697 B1 | | 9/2001 | Roberts |
| D459,814 S | | 7/2002 | Lee et al. |
| 6,516,227 B1 | | 2/2003 | Meadows et al. |
| 6,580,948 B1 | | 6/2003 | Haupert et al. |
| 6,593,528 B1 | | 7/2003 | Franklin-Lees et al. |
| 6,622,048 B1 | | 9/2003 | Mann et al. |
| 6,740,075 B1 | | 5/2004 | Lebel et al. |
| 2002/0016568 A1 | | 2/2002 | Lebel et al. |
| 2002/0019606 A1 | | 2/2002 | Lebel et al. |

(Continued)

FOREIGN PATENT DOCUMENTS

EP 0402251 8/1994

(Continued)

*Primary Examiner*—George Manuel
(74) *Attorney, Agent, or Firm*—Benner & Witcoff, Ltd.

(57) ABSTRACT

Disclosed is a universal connector for connecting component devices of an implantable medical treatment system. The universal connector includes a male and a female interface adapted to connectively mate two devices of the implantable medical treatment system. A locking flange and recess are provided, as well as a locking shoulder and ridge combination, to securely connect the mated male and female interfaces. When mated and securely joined, the universal connector of the present invention allows a device of the implantable medical treatment system to interface with any other device of the implantable medical treatment system for simplified handling and bi-directional communications.

25 Claims, 6 Drawing Sheets

U.S. PATENT DOCUMENTS

| | | |
|---|---|---|
| 2002/0049480 A1 | 4/2002 | Lebel et al. |
| 2002/0058906 A1 | 5/2002 | Lebel et al. |
| 2002/0065454 A1 | 5/2002 | Lebel et al. |
| 2002/0065509 A1 | 5/2002 | Lebel et al. |
| 2002/0065540 A1 | 5/2002 | Lebel et al. |
| 2003/0135246 A1 | 7/2003 | Mass et al. |
| 2003/0174066 A1 | 9/2003 | Goetz et al. |
| 2003/0174069 A1 | 9/2003 | Goetz et al. |
| 2003/0176807 A1 | 9/2003 | Goetz et al. |
| 2003/0177031 A1 | 9/2003 | Malek |

FOREIGN PATENT DOCUMENTS

| | | |
|---|---|---|
| EP | 0614382 | 3/1996 |
| EP | 0918556 | 6/1999 |
| EP | 1134003 | 9/2001 |
| GB | 1595923 | 8/1981 |
| WO | WO 01/36027 | 5/2001 |

* cited by examiner

METHOD AND APPARATUS FOR CONNECTING VARIOUS IMPLANTABLE MEDICAL TREATMENT SYSTEM COMPONENT DEVICES

FIELD OF THE INVENTION

The present invention generally relates to implantable medical device systems. More particularly, this invention relates to uniform interfaces for connecting component devices of an implantable medical treatment system, including telemetry modules of wired or wireless physician/patient programmers, magnet housings, external neural stimulators, patient chargers, and various other programming system component devices.

BACKGROUND OF THE INVENTION

The medical device industry produces a wide variety of electronic and mechanical devices for treating patient medical conditions. Depending upon the medical condition, medical devices can be surgically implanted or connected externally to the patient receiving treatment. Physicians use medical devices alone or in combination with drug therapies to treat patient medical conditions. For some medical conditions, medical devices provide the best, and sometimes the only, therapy to restore an individual to a more healthful condition and a fuller life.

Implantable medical devices are commonly used today to treat patients suffering from various ailments. Implantable medical devices can be used to treat any number of conditions such as pain, incontinence, movement disorders such as epilepsy and Parkinson's disease, and sleep apnea. Additional therapies appear promising to treat a variety of physiological, psychological, and emotional conditions. As the number of implantable medical device therapies has expanded, greater demands have been placed on the implantable medical device.

These devices provide treatment therapy by delivering electrical stimulation or drugs to various portions of the body and include, for example without limitation, neurostimulators, drug delivery devices, pacemakers, defibrillators, and cochlear implants. In the case of providing electrical stimulation, one or more electrodes are implanted within the body. A physician uses an external neural stimulator (ENS) connected to provide electrical energy to the electrodes and establish effective treatment parameters. Once efficacious treatment settings have been determined, an implantable neurostimulator (INS) (also known as an Implantable Pulse Generator (IPG)) replaces the ENS, is connected to the electrodes, and is implanted within the patient's body. In the case of providing drugs, a pump is implanted within the body. The pump is coupled to a catheter that delivers drugs to select portions of the body. Patients can be implanted with both INS and pump devices, or combination devices. INS and pump devices can be programmed and recharged while implanted within a patient to adjust treatment therapies over time without invasive surgery.

A physician programmer, typically a computer with associated electronics, can communicate with the ENS, INS, and pump devices using telemetry. A telemetry module is linked to the physician programmer with a cable or by wireless methods. A patient programmer and a patient charger can also communicate with implanted treatment devices, as well as with the physician programmer, via wired or wireless links. The physician or patient may want devices of the treatment system to communicate with one another via telemetry for any number of reasons including, for example, to recharge a power supply of the implanted device, to fine tune the therapy program, to exchange diagnostic data between devices, to account for changes in the disease being treated, or to account for migration of the implanted lead or catheter.

Known systems for programming a medical device have a number of disadvantages. In particular, many implanted pumps must be activated for programming by the presence of a strong magnet. Such a magnet is typically built into the telemetry module used to program the pump. In contrast, an INS is sometimes activated or deactivated by a strong magnet and therefore, a single telemetry module could not be used to communicate with both an INS and an implantable pump. In another example of known limitations, a physician programmer, patient programmer, ENS, patient charger, and other component devices of the telemetry programming system could not be uniformly connected to communicate with one another via telemetry. This limitation is especially problematic because telemetrically communicating devices must be held in close proximity to one another, and handling multiple devices during medical treatment is cumbersome. In yet another example, when the power supply of the implanted device needs to be recharged, the patient must physically hold the telemetry module close to his/her body. This can be of great inconvenience when it takes on the order of hours to fully recharge the power supply. These limitations required physicians and patients to use multiple programming devices, thereby increasing the cost, time, and complexity of handling and operating the various component devices of an implantable medical treatment system.

BRIEF SUMMARY OF THE INVENTION

The universal connector of the present invention allows component devices of a programming system to be efficiently and securely connected to one another. In an exemplary embodiment, a female interface of the universal connector is included on the telemetry module of a hand-held physician programmer. Correspondingly, a male interface of the universal connector is included on a hand-held patient programmer, on a magnet housing, on an ENS, on a patient charger, and on any other device of the programming system that is advantageously connected to the telemetry module of the physician programmer. By mating the male interface to the female interface, two devices of the programming system can be securely connected together. It is not critical to the invention which device carries the male or female interface, so long as the two devices to be connected carry different, interlocking interfaces. Thus, for example, a magnet housing having a male interface connector can be connected to a telemetry module for programming an implanted pump, and the magnet can be removed when the same telemetry module is used to program an INS. Likewise, the same telemetry module can be directly connected to a patient programmer or to an ENS.

The universal connector of the present invention is easy to operate, provides visual cues about its operation, and produces positive tactile feedback when a secure connection is achieved. The connector is durable and compact, allowing a single telemetry module design to connect with any other element of the programming system. The universal connector of the present invention thus allows a telemetry module to interface with any number of devices and accomplish the objectives of previously separate units. Furthermore, the connector of the present invention insures that communicating devices will be securely held in proximity to one another for effective telemetry. Advantageously, patient and physician only need to use one programming device. In addition, the connector of the present invention allows components to be more conveniently handled, effectively allowing a user to hold two component devices in one hand, freeing the other hand for other activities such as using the programmer, writing, or attending to the patient, among others.

BRIEF DESCRIPTION OF THE DRAWINGS

These and other advantages and features of the invention will become apparent upon reading the following detailed description and referring to the accompanying drawings in which like numbers refer to like parts throughout and in which.

DETAILED DESCRIPTION OF THE INVENTION

Figure 1A:
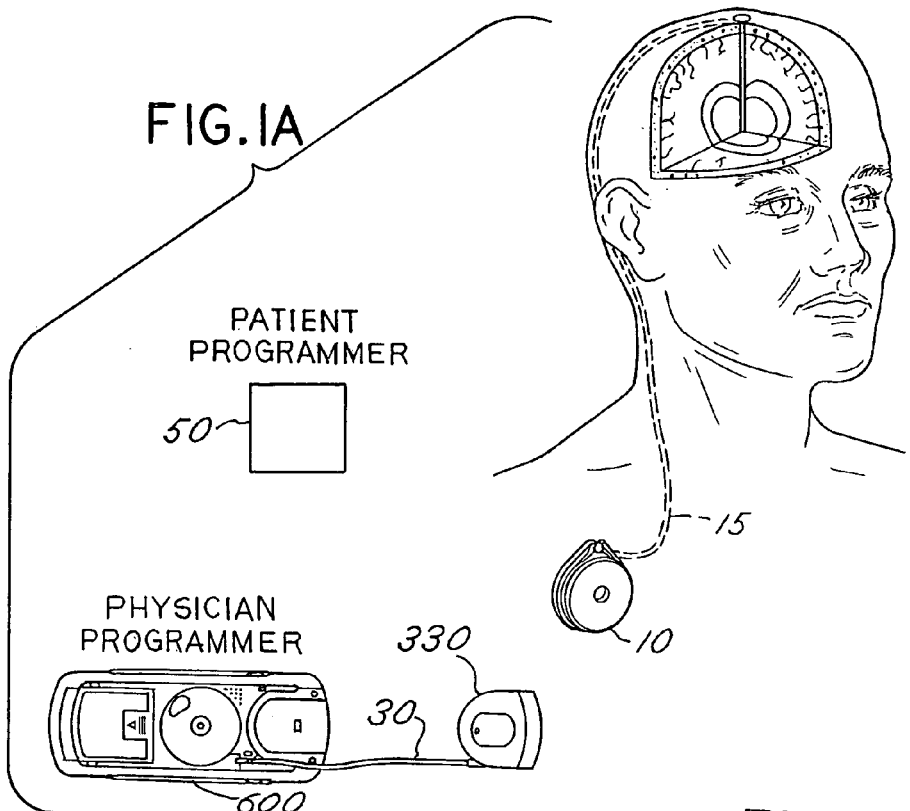
FIG. 1A is a representation of an implanted medical pump in relation to a hand-held physician programmer and a patient programmer.

FIG. 1A illustrates the relationship between physician programmer 600, patient programmer 50, and implanted pump 10 in accordance with one embodiment of the present invention. As shown, telemetry module 330 is linked to physician programmer 600 through cable 30, although one skilled in the art will appreciate that telemetry module 330 can be designed to communicate with physician programmer 600 by wired or wireless methods. Patient programmer 50 and physician programmer 600 can advantageously communicate with one another via telemetry. Likewise, patient programmer 50 and physician programmer 600 can communicate with implanted pump 10 via telemetry. As shown, implanted pump 10 is connected to catheter 15 and may be used to deliver a treatment drug, held in a reservoir within the pump, to a target area of a patient's body. A physician or patient may wish to establish bi-directional links between the treatment devices for any number of reasons, including to exchange data, to adjust therapy programs, or to recharge the implanted pump. As one skilled in the art will recognize, it would be advantageous to uniformly connect telemetry head 330 to a magnet to facilitate communications with an implanted pump, or to connect telemetry head 330 directly to patient programmer 50. Also, attaching a magnet to telemetry head 330 allows the telemetry head to be held in place against a patient's skin by magnetic attraction to pump 10 during lengthy programming or charging sessions.

Figure 1B:
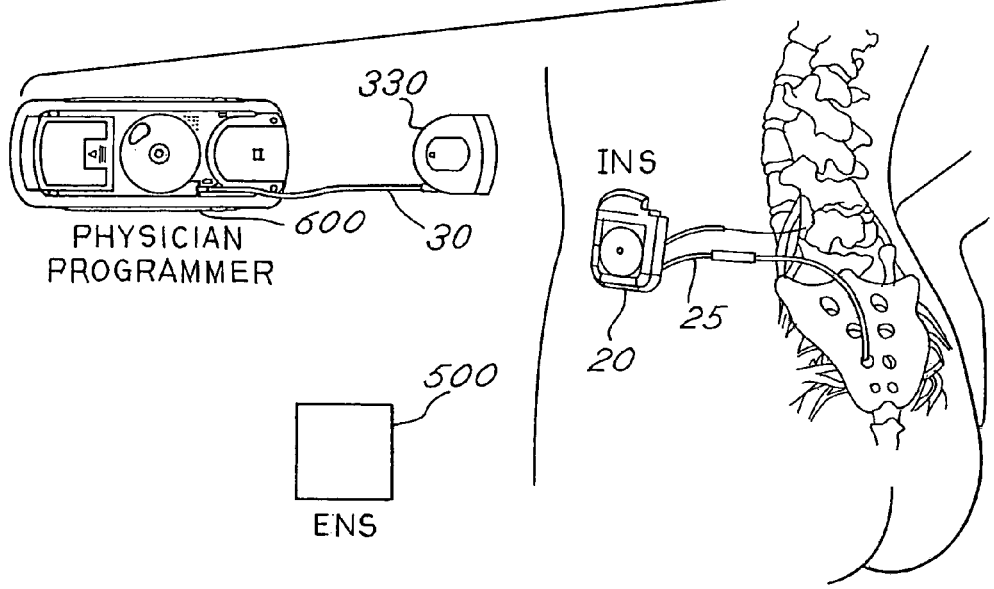
FIG. 1B is a representation of an INS in relation to a hand-held physician programmer and an ENS.

FIG. 1B illustrates the relationship between physician programmer 600, ENS 500, and INS 20 in accordance with another embodiment of the present invention. One or more electrical leads 25 are implanted within a patient, for example, to electrically stimulate regions of the spinal cord and thereby relieve pain. A physician uses ENS 500, connected to leads 25, to determine an efficacious treatment therapy. Once a therapy is established, ENS 500 is disconnected, and INS 20 is connected to leads 25 and implanted within the body. As one skilled in the art will recognize, it would be advantageous to be able to uniformly connect telemetry head 330 to ENS 500 to facilitate programming and communications between the devices. Likewise, it would be advantageous to be able to communicate with INS 20 using the same telemetry module used to program an implanted pump like pump 10 shown in FIG. 1A, without a magnet attachment connected to the telemetry module.

Figure 2A:
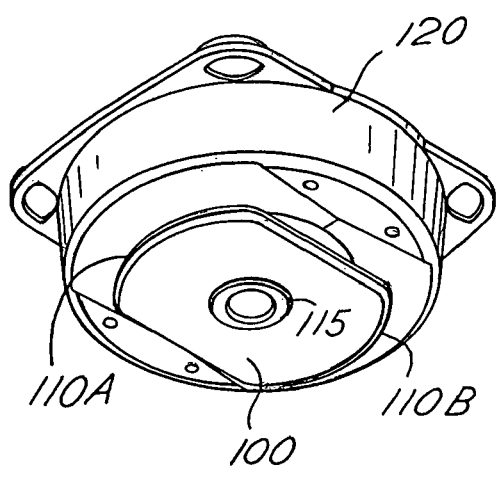
FIG. 2A is a front side view of a male connector interface of the present invention mounted to a magnet housing used in programming an implanted medical pump.
Figure 2B:
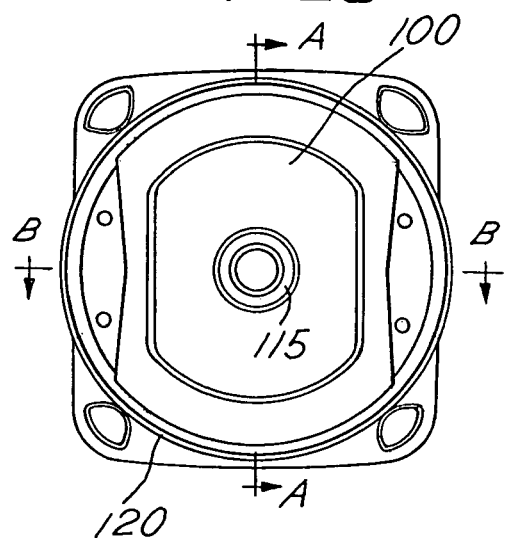
FIG. 2B is a frontal view of the male connector interface of FIG. 2A.
Figure 2C:
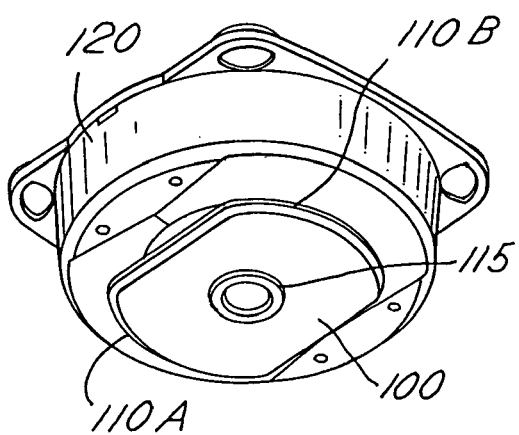
FIG. 2C is a front side view of the male connector interface of FIG. 2A rotated 90-degrees.
Figure 2D:
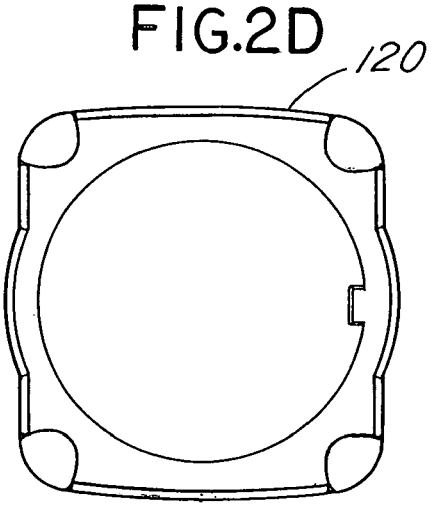
FIG. 2D is a back view of the magnet housing of FIGS. 2A–2C.

The uniform connector of the present invention allows the various component devices of the programming system of FIGS. 1A and 1B to be advantageously connected. Those skilled in the art will appreciate, however, that the present invention can be used in conjunction with any implanted medical devices, including, for example without limitation, neurostimulators, drug delivery devices, pacemakers, defibrillators, and cochlear implants, and that FIGS. 1A and 1B serve merely as examples of how the present invention can be used. FIGS. 2A–C illustrate male connector interface 100, including at least one interface flange 110A and 110B. Male connector interface 100 further includes bearing surface 115. Male interface 100 is shown on magnet housing 120. Although FIGS. 2A–C show male interface 100 in relation to magnet housing 120, interface 100 can be used in relation to any other device of the programming system so long as the two devices to be connected carry different, interlocking interfaces, i.e., one male, one female. FIG. 2D illustrates the reverse side of magnet housing 120, which is brought into contact with a patient's skin or clothing.

Figure 3A:
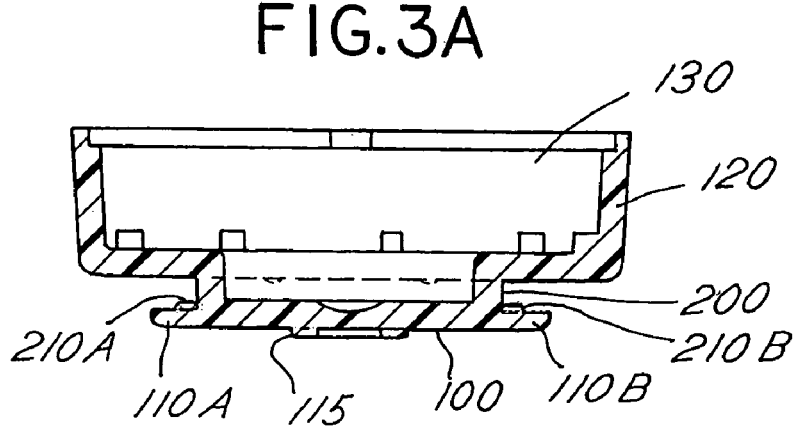
FIG. 3A is a cross-sectional view of the male interface connector of FIG. 2B taken along line B—B.
Figure 3B:
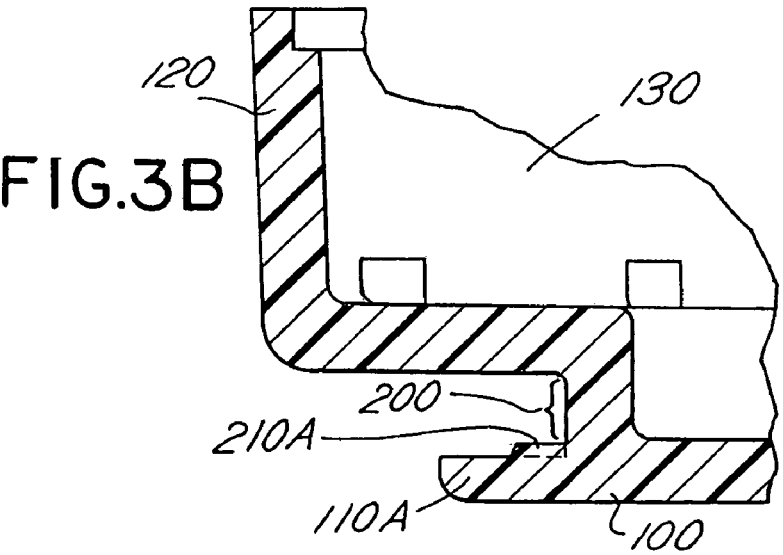
FIG. 3B is an enlarged, partial, cross-sectional view of the male interface connector of FIG. 3A.

FIG. 3A illustrates a cross-section view of male connector interface 100 taken along line A—A of FIG. 2B. FIG. 3B shows a detail of FIG. 3A. In FIGS. 3A and 3B, Male interface 100 is shown protruding from magnet housing 120 on shaft 200. The shaft 200 of male connector interface 100 allows flanges 110A and 110B to be inserted into female interface 300, described below. Flanges 110A and 110B further include at least one shoulder 210A and 210B. As described further below, shoulders 210A and 210B lockingly engage female interface 300 and provide a tactile indication when a secure connection between the male and female interfaces has been achieved. By tensioning the interface of male interface 100 and female interface 300, bearing surface 115 works in conjunction with shoulders 210A and 210B to insure a positive tactile indication when a secure connection is achieved. Bearing surface 115 further provides a smooth surface on which male interface 100 can rotate within female interface 300, as described below.

Figure 3C:
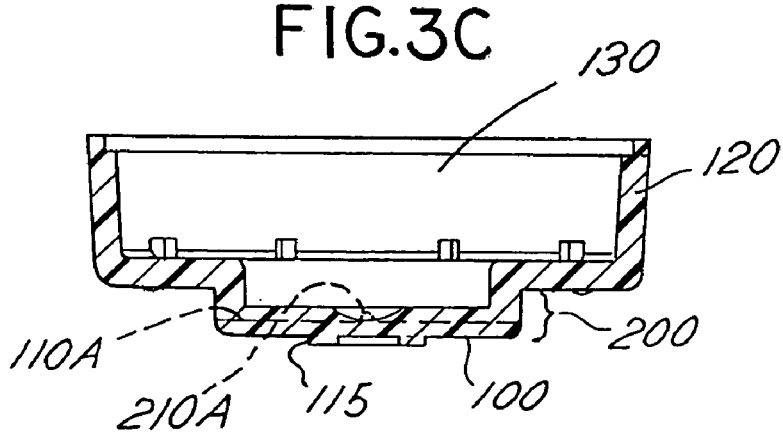
FIG. 3C is a cross-sectional view of the male interface connector of FIG. 2B taken along line C—C.

FIG. 3C illustrates a cross-section of male connector interface 100 taken along line B—B of FIG. 2B. Referring now to FIGS. 3A–3C as a group, shoulder 210A is shown generally centered on flange 110A and abutting shaft 200. Magnet housing 120 includes magnet receptacle 130 wherein a magnet (not shown) can be enclosed to create a magnetic field around the magnet housing. In practice, housing 120 contains a magnet capable of interacting with an implantable pump such as the device shown in U.S. Pat. No. 4,692,147 (Duggan), assigned to Medtronic, Inc., Minneapolis, Minn., and commercially available as the Synchromed infusion pump, both of which are incorporated by reference. Housing 120 is connected to a telemetry module of a physician programmer through the mating of male connector interface 100 and female connector interface 300, described below. When housing 120 is moved near to a patient's implanted pump, the pump is activated for programming in response to the magnetic field generated by the magnet enclosed within housing 120 and telemetry can be initiated. Further, the magnetic attraction between the magnet of housing 120 and a magnet of an implanted pump holds telemetry head 330 of FIG. 1A in place while the physician programmer is communicating with the implanted pump. In this way, the physician or patient is freed from having to hold the telemetry head in place during lengthy programming or recharging sessions.

Figure 4A:
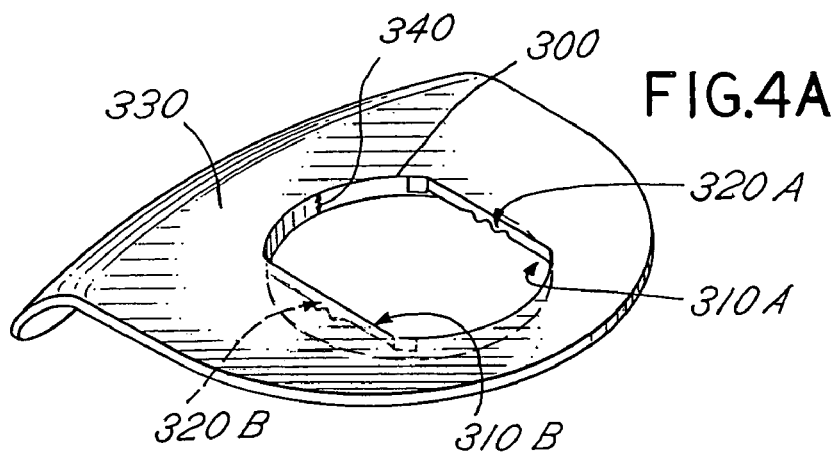
FIG. 4A is a front side view of a female connector interface of the present invention mounted to a surface of a telemetry module used to communicate with other component devices of an implantable medical treatment system.
Figure 4B:
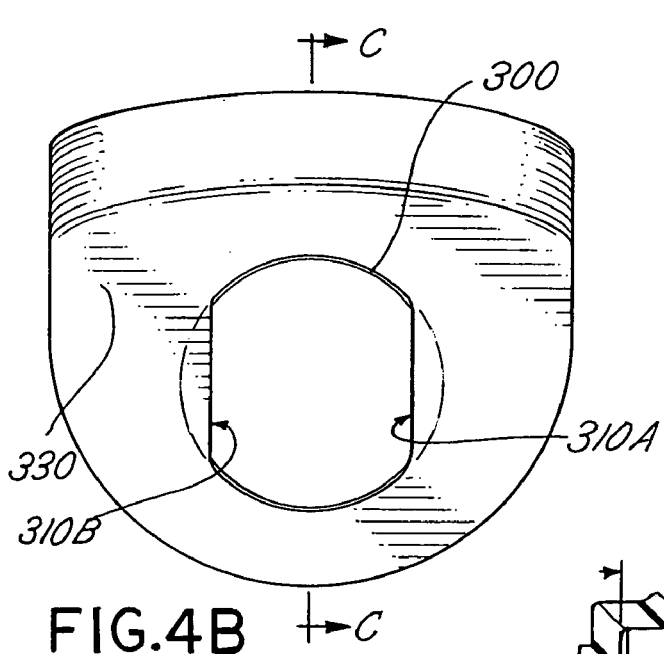
FIG. 4B is a front view of the female connector interface of FIG. 4A.

FIGS. 4A and 4B illustrate female connector interface 300, including at least one overhanging recess 310A and 310B and at least one locking ridge 320A and 320B thereupon. When connected, shaft 200 of male interface 100 is inserted into depth 340 of female interface 300. Magnet housing 120 is turned to rotate male interface 100 90-degrees in either direction and thereby slide interface flanges 110A and 110B into recesses 310A and 310B. Bearing surface 115 on male interface 100 (shown in FIGS. 2A–2C) and close tolerances allow for a secure and reliable fit. Male interface 100 is thereby connectively mated to female interface 300. Although shown on telemetry module 330, female interface 300 can be used in relation to any other device of the programming system so long as the two devices to be connected carry different, interlocking interfaces, i.e., one male, one female.

Figure 4C:
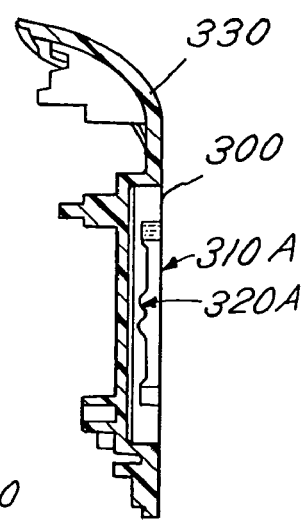
FIG. 4C is a partial, side, cross-sectional view of the female connector interface of FIG. 4B taken along line C—C.
Figure 4D:
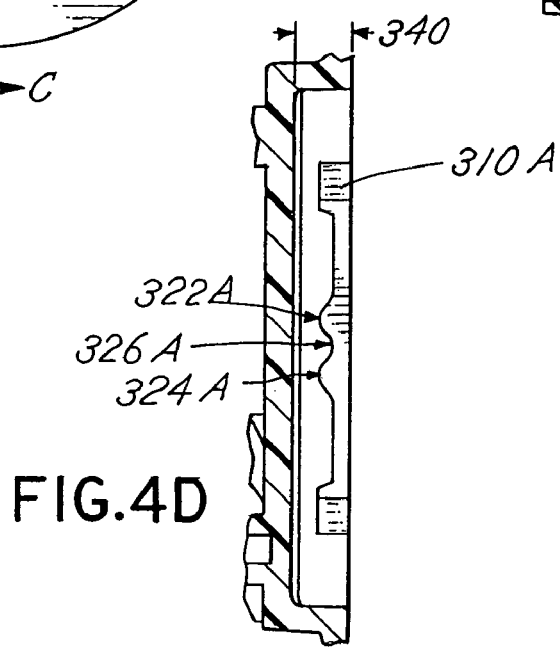
FIG. 4D is an enlarged, partial, cross-sectional view of the female interface connector of FIG. 4C.

FIG. 4C illustrates a cross-section of female interface 300 taken along line C—C of FIG. 4B. FIG. 4D shows a detail of FIG. 4C. As seen in FIGS. 4C and 4D, locking ridge 320A consists of at least two peaks 322A, 324A, and valley 326A. Although not shown in this cross-section, locking ridge 320B includes similar peaks 322B, 324B, and valley 326B. Referring now to FIGS. 2A–4D as a group, in practice, shoulders 210A and 210B engage the peaks and valleys of locking ridge 320A and 320B when male interface 100 is rotated to slide interface flanges 110A and 110B within recesses 310A and 310B. The interaction of shoulders 210A and 210B with locking ridges 320A and 320B, in conjunction with bearing surface 115, provides a locking stop position in the rotation of shaft 200 and a tactile indication to a user that male interface 100 has securely engaged female interface 300. In this way, any variety and combination of component devices of an implantable medical device programming system, including but not limited to a telemetry module of a physician programmer, a patient programmer, an ENS, a magnet housing, or a patient charger, can be securely connected to one another, so long as the two devices to be connected carry different, interlocking interfaces, i.e., one male and one female.

Figure 5A:
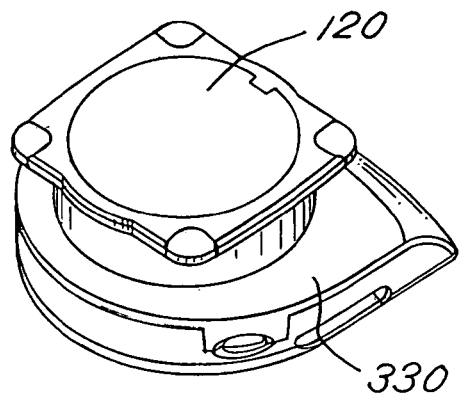
FIG. 5A is a front side view of a magnet housing connected to a telemetry module via the uniform interface of the present invention.
Figure 5B:
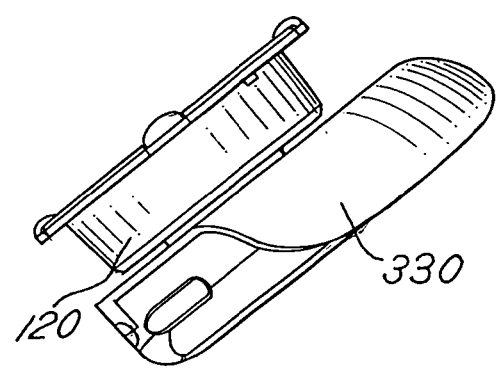
FIG. 5B is a side view of FIG. 5A.

FIGS. 5A and 5B illustrate a magnet housing 120 connected to telemetry module 330 via the uniform connector interface of the present invention. In this configuration, telemetry module 330 can be used to program an implanted pump. Alternatively, magnet housing 120 can be removed, and telemetry module 330 can be used to program an INS.

Figure 6A:
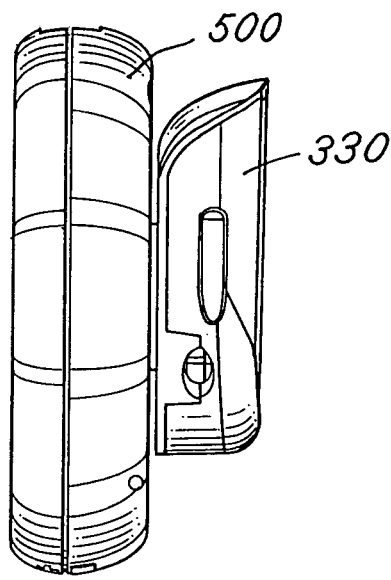
FIG. 6A is a side view of an external neural stimulator connected to a telemetry module via the uniform connector of the present invention.
Figure 6B:
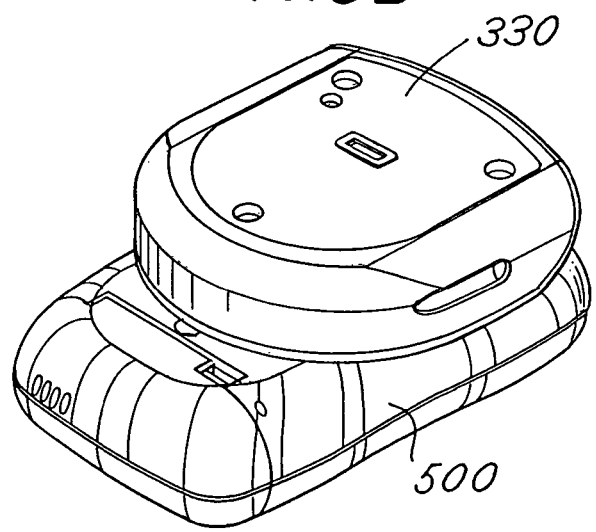
FIG. 6B is a front side view of FIG. 6A.

FIGS. 6A and 6B illustrate a telemetry module 330 connected to an ENS unit 500 via the uniform connector interface of the present invention. In this configuration, a bi-directional communications link exists between the telemetry module 330 and the ENS 500 to enable a physician programmer like physician programmer 600 shown in FIG. 1B to program the ENS with treatment parameters via the bi-directional communications link. The treatment parameters may be provided singly or in a batch, or the parameters may be provided one at a time in a real-time interactive mode. The physician programmer may also upgrade software or operating system of the ENS 500 via this bi-directional communications link. The ENS 500 may also provide certain diagnostic information back to the physician programmer including, for example, parameter settings (e.g., stimulation frequency, stimulation pulse amplitude, stimulation pulse width, electrode configuration, etc.), patient diagnostic data (e.g., usage data), system diagnostic data (e.g., battery status, estimated longevity of implanted device, lead system integrity, load impedance, etc.), data on device usage, data regarding the last programmer/ENS session, the state of the device, configuration of an INS (e.g., simple or complex patient user interface), whether a valid communication channel exists, and the like.

Figure 7:
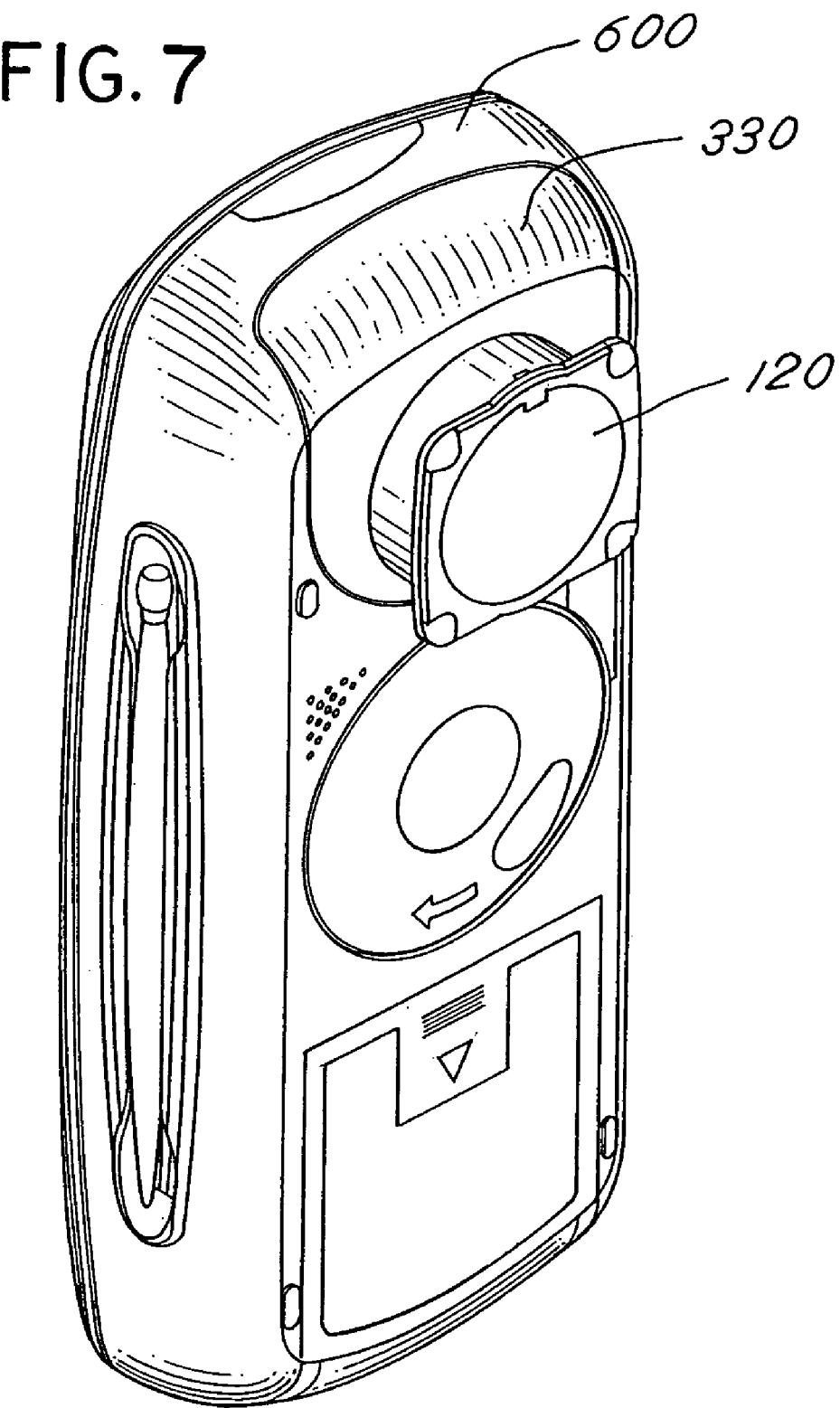
FIG. 7 is a back side view of a magnet housing connected to a telemetry module via the uniform interface of the present invention, where the telemetry module is cradled in a physician programmer.

FIG. 7 illustrates magnet housing 120 connected to telemetry module 330 via the uniform connector interface of the present invention, and where telemetry module 330 is docked to physician programmer 600.

Referring now to FIGS. 1A, 1B, and 5A–7 as a group, it is apparent that other component devices of the implantable medical treatment system can be connected via the uniform connector interface of the present invention. For example, a patient programmer, patient charger, or even other telemetry modules can be connected to telemetry module 330 so long as each device to be connected includes a different uniform connector interface, i.e., one male and one female. In this way, a single physician programmer can securely connect to any other device of the system and exchange any manner of information via a bi-directional communications link. Among other advantages, the connected devices can be easily handled as one device and are securely placed in close proximity to one another for effective telemetry.

What is claimed is:

1. A connection system for joining external components of an implantable medical device system, the connection system comprising:
    a first external medical device component;
    a second external medical device component;
    a male connector shaft on the first external medical device component;
    at least one flange located on the male connector shaft;

a female connector interface on the second external medical device component; and at least one recess located on the female connector interface configured to couple with the flange of the male connector shaft, wherein at least one of the first external medical device component and the second external medical device component operatively communicates with an implanted medical device of the implantable medical device system via telemetry.

2. The connections system of claim 1 wherein the flange is located on a distal end of the male connector shaft.

3. The connections system of claim 1 wherein the telemetry between one of the first external medical device component and the second external medical device component, and the implanted medical device is facilitated by at least one intermediate device.

4. A connection system for joining external components of an implantable medical device system, the connection system comprising:
    a first external medical device component;
    a second external medical device component;
    a male connector shaft on the first external medical device component;
    at least one flange located on the male connector shaft;
    a female connector interface on the second external medical device component; and
    at least one recess located on the female connector interface configured to couple with the flange of the male connector shaft, wherein the first external medical device component is selected from the group consisting of an external neural stimulator, a patient charger, a patient programmer, and a magnet housing.

5. A connection system for joining external components of an implantable medical device system, the connection system comprising:
    a first external medical device component;
    a second external medical device component;
    a male connector shaft on the first external medical device component;
    at least one flange located on the male connector shaft;
    a female connector interface on the second external medical device component; and
    at least one recess located on the female connector interface configured to couple with the flange of the male connector shaft, wherein the first external medical device component is a physician programmer telemetry module.

6. A connection system for joining external components of an implantable medical device system, the connection system comprising:
    a first external medical device component;
    a second external medical device component;
    a male connector shaft on the first external medical device component;
    at least one flange located on the male connector shaft;
    a female connector interface on the second external medical device component; and
    at least one recess located on the female connector interface configured to couple with the flange of the male connector shaft, wherein the first external medical device component is a first telemetry module and the second external medical device component is a second telemetry module.

7. A connector for joining a first external module and a second external modules of an implanted medical device, comprising in combination:
    a male connector interface including a shaft, wherein the male connector is associated with one of the external modules of the implantable medical device system;
    at least one flange located on the shaft;
    at least one locking shoulder located on the flange;
    a female connector interface, wherein the female connector is associated with another of the external modules of the implantable medical device system;
    at least one recess located on the female connector interface adapted to couple with the at least one flange on the shaft; and
    a locking ridge located in the recess adapted to engage the locking shoulder of the flange of the male connector interface, wherein the male connector interface is mounted on the first external module and the female connector interface is mounted on the second external module, wherein one of the first and second external modules is configured to be communicably connected to the implanted medical device.

8. The connector of claim 7 wherein the flange is located on a distal end of the shaft.

9. The connector of claim 7 wherein one of the first and second external modules is configured so the connection to the implanted medical device is direct.

10. A connector for joining a first external module and a second external modules of an implanted medical device, comprising in combination:
    a male connector interface including a shaft, wherein the male connector is associated with one of the external modules of the implantable medical device system;
    at least one flange located on the shaft;
    at least one locking shoulder located on the flange;
    a female connector interface, wherein the female connector is associated with another of the external modules of the implantable medical device system;
    at least one recess located on the female connector interface adapted to couple with the at least one flange on the shaft; and
    a locking ridge located in the recess adapted to engage the locking shoulder of the flange of the male connector interface, wherein the male connector interface is mounted on the first external module and the female connector interface is mounted on the second external module, wherein the first module is selected from the group consisting of an external neural stimulator, a patient charger, a patient programmer, and a magnet housing.

11. A connector for joining a first external module and a second external modules of an implanted medical device, comprising in combination:
    a male connector interface including a shaft, wherein the male connector is associated with one of the external modules of the implantable medical device system;
    at least one flange located on the shaft;
    at least one locking shoulder located on the flange;
    a female connector interface, wherein the female connector is associated with another of the external modules of the implantable medical device system;
    at least one recess located on the female connector interface adapted to couple with the at least one flange on the shaft; and
    a locking ridge located in the recess adapted to engage the locking shoulder of the flange of the male connector interface, wherein the male connector interface is mounted on the first external module and the female connector interface is mounted on the second external module, wherein the first module comprises a physician programmer telemetry module.

12. A method of connecting external component devices of an implantable medical treatment system, the method comprising in combination the steps of:
providing a first external device of the implantable medical treatment system with a male connector interface having at least one flange;
providing a second external device of the implantable medical treatment system with a female connector interface having at least one recess;
inserting the male connector interface of the first external device into the female connector interface of the second external device; and
rotating the male and female connector interfaces in relation to one another to connectively engage the flange of the male connector interface with the recess of the female connector interface.

13. The method of claim 12, wherein the step of rotating causes a relative rotation between the male connector interface and the female connector interface in the range of 1 to 179 degrees.

14. A system for use in treating a patient with electrical stimulation; the system comprising:
an external neural stimulator, the external neural stimulator having a first connector interface;
a telemetry module, the telemetry module including a second connector interface, the second connector interface configured to connectively mate with the first connector interface wherein the first connector interface comprises one of a flange mounted on a shaft, or a recess, and the second connector interface comprises the other of the flange mounted on a shaft, or a recess; and
a programmer in communication with the telemetry module.

15. The system of claim 14, wherein the first connector interface includes the flange mounted on the shaft and the second connector interface includes the recess.

16. The system of claim 14, wherein the second connector interface includes the flange mounted on the shaft and the first connector interface includes the recess.

17. The system of claim 14, wherein the communication between the programmer and the telemetry module is wireless.

18. A system for use in communicating between external components of an implanted medical treatment system, comprising:
a first external component having a first connector interface;
a first telemetry module have a second connector interface, the second connector interface configured to connect with the first connector interface via the interaction between a flange located on a shalt and a corresponding recess; and
a second external component connected to a second telemetry module, whereby the second component communicates in a wireless manner with the first telemetry module via the second telemetry module.

19. The system of claim 18, wherein the first component consist of one of the following: an external neural stimulator, a patient programmer, a patient charger or a magnet housing.

20. The system of claim 18, wherein the second external component includes a first connector interface and the second telemetry module includes a second connector interface, and the first connector interface on the second external component and the second connector interface on the second telemetry module are configured to connect together via the interaction between a flange located on a shaft and a corresponding recess.

21. A system for use in signaling an implanted medical device, comprising:
an external medical device component configured to provide a first signal
an external telemetry module configured to receive the first signal and further configured to transmit a second signal to the implanted device;
a first connector interface mounted on the external telemetry module; and
a magnet housing having a second connector interface configured to mate with the first connector interface of the external telemetry module, whereby the first external medical device component and the external telemetry module can be utilized with or without the magnet housing.

22. The system of claim 21, wherein the first connector interface includes a shaft and a flange mounted on the shaft and the second connector interface includes a recess configured to couple with the flange on the shaft of the first connector interface.

23. The system of claim 21, wherein the second connector interface includes a shaft and a flange mounted on the shaft and the first connector interface includes a recess configured to couple with the flange on the shaft of the second connector interface.

24. The system of claim 21, wherein the first connector interface further includes a locking shoulder located on the flange and the second connector interface further includes a locking ridge located on the recess, the locking ridge configured to engage the locking shoulder of the flange of the first connector interface 25. The system of claim 21, wherein the medical device component is a patient programmer.

* * * * *

UNITED STATES PATENT AND TRADEMARK OFFICE
CERTIFICATE OF CORRECTION

PATENT NO. : 7,010,355 B2  
APPLICATION NO. : 10/098279  
DATED : March 7, 2006  
INVENTOR(S) : David Warren Lee Page 1 of 1

It is certified that error appears in the above-identified patent and that said Letters Patent is hereby corrected as shown below:

<u>Column 7</u>
Line 61, "connector shalt" should read -- connector shaft --.

<u>Column 9</u>
Line 54, "on a shalt" should read -- on a shaft --.

Signed and Sealed this

Tenth Day of November, 2009

David J. Kappos
*Director of the United States Patent and Trademark Office*